US00PP26294P2

(12) United States Plant Patent
Hanes

(10) Patent No.: US PP26,294 P2
(45) Date of Patent: Jan. 5, 2016

(54) ***PELARGONIUM* PLANT NAMED 'PEQZ0007'**

(50) Latin Name: *Pelagonium interspecific*
Varietal Denomination: PEQZ0007

(71) Applicant: Syngenta Crop Protection AG, Basel (CH)

(72) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 73 days.

(21) Appl. No.: 13/998,128

(22) Filed: Oct. 4, 2013

(51) Int. Cl.
*A01H 5/02* (2006.01)

(52) U.S. Cl.
USPC ..... Plt./329

(58) Field of Classification Search
USPC ..... Plt./325, 328, 329
See application file for complete search history.

*Primary Examiner* — Keith Robinson
(74) *Attorney, Agent, or Firm* — Joshua L. Price

(57) ABSTRACT

A new *Pelargonium* plant named 'PEQZ0007' particularly distinguished by the large light red-purple flowers with a bold red-purple large-sized splash pattern, fairly large inflorescences, relatively long peduncles, medium green foliage without zonation, good branching and rounded plant habit.

1 Drawing Sheet

Latin name of the genus and species of the plant claimed: *Pelargonium interspecific.*

Varietal denomination: 'PEQZ0007'.

BACKGROUND OF THE NEW PLANT

The present invention comprises a new *Pelargonium*, botanically known as *Pelargonium interspecific*, and hereinafter referred to by the variety name 'PEQZ0007'.

'PEQZ0007' is a product of a planned breeding program. The new cultivar 'PEQZ0007' has large light red-purple flowers with a bold red-purple large-sized splash pattern, fairly large inflorescences, relatively long peduncles, medium green foliage without zonation, good branching and rounded plant habit.

'PEQZ0007' originates from a hybridization made in September 2007 in a greenhouse in Gilroy, Calif. The female parent was an unpatented, proprietary plant identified as '10536-1' with white flowers with a slight splash pattern and the flower size and splash pattern is smaller when compared to 'PEQZ0007'.

The male parent of 'PEQZ0007' was an unpatented, proprietary plant, identified as '10499-1' with pink flowers with a splash pattern. 'PEQZ0007' is more free flowering and has a more rounded plant habit when compared to '10499-1'. The resultant seed was sown in August 2008.

'PEQZ0007' was selected as one flowering plant within the progeny of the stated cross in November 2008 in a greenhouse in Gilroy, Calif.

The first act of asexual reproduction of 'PEQZ0007' was accomplished when vegetative cuttings were propagated from the initial selection in November 2008 in a greenhouse in Gilroy, Calif.

BRIEF SUMMARY OF INVENTION

Horticultural examination of plants grown from cuttings of the plant initiated in November 2008 in Gilroy, Calif., and continuing thereafter, has demonstrated that the combination of characteristics as herein disclosed for 'PEQZ0007' are firmly fixed and are retained through successive generations of asexual reproduction.

'PEQZ0007' has not been observed under all possible environmental conditions. The phenotype may vary significantly with variations in environment such as temperature, light intensity, and day length.

Plant Breeder's Rights for this cultivar were applied for in Canada on Nov. 9, 2012 (12-7790) and at Community Plant Variety Office on Jun. 4, 2013 (2013/1513). 'PEQZ0007' has not been made publicly available more than one year prior to the filing of this application.

The following traits have been repeatedly observed and are determined to be basic characteristics of the new variety. The combination of these characteristics distinguishes this *Pelargonium* as a new and distinct variety.

BRIEF DESCRIPTION OF THE PHOTOGRAPHS

The accompanying photographic drawing shows typical flower and foliage characteristics of 'PEQZ0007' with colors being as true as possible with an illustration of this type.

Figure 1:
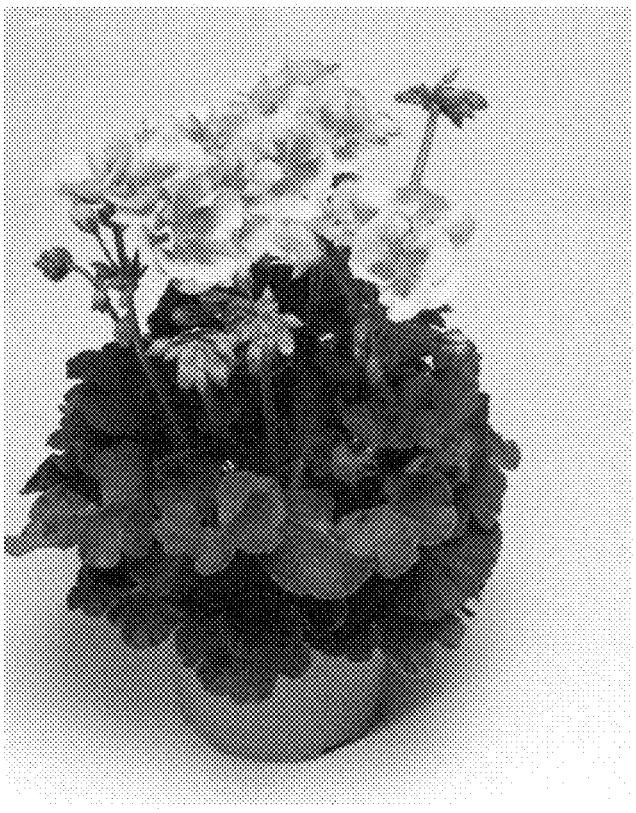
Figure 2:
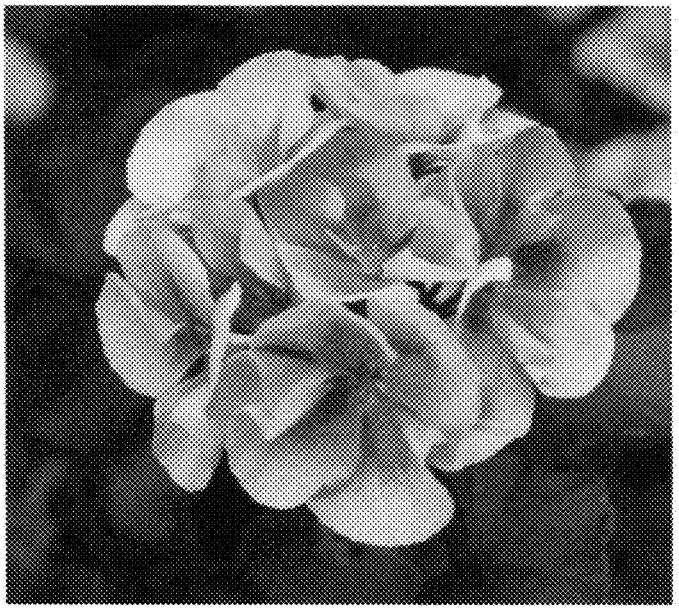

The photographic drawing shows in FIG. 1 a flowering plant of the new variety and in FIG. 2 a close-up of an inflorescence.

DETAILED BOTANICAL DESCRIPTION

The plant descriptions and measurements were taken in Gilroy, Calif. in August under natural light. These plants were approximately 25 weeks old and were grown in 6 inch pots, first in a greenhouse and later outdoors.

The plants shown in the photographs were about 15-18 weeks old, growing in a 6 inch pot in a greenhouse. The photographs were taken inside a greenhouse in May in Enkhuizen, The Netherlands.

Color references are made to The Royal Horticultural Society Colour Chart (R.H.S.) 2001.

TABLE 1

DIFFERENCES BETWEEN THE NEW VARIETY 'PEQZ0007' AND A MOST SIMILAR VARIETY

| | 'PEQZ0007' | 'Auld Pikegs' (U.S. Plant Pat. No. 20,481) |
|---|---|---|
| Branching habit: | More branches | Fewer branches |
| Flowering habit: | Is more free-flowering | Is less free-flowering |
| Plant habit: | Has tighter plant habit | Has a more open plant habit |

Plant:

*Form, growth and habit.*—Upright, outwardly spreading and rounded growth habit. Vigorous, well branched and grows well in sun or semi-shade.

*Plant height.*—19-21.0 cm.

*Plant height (inflorescence included)*: 21-24.0 cm.

*Plant width.*—35-40.0 cm.

Roots:

*Number of days to initiate roots.*—15-18 days at about 22 degrees C.

*Number of days to produce a rooted cutting.*—21-24 days at 22 degrees C.

*Type.*—Fine, fibrous, free branching.

*Color.*—RHS N155B but whiter.

Foliage:

*Immature leaf, color upper surface.*—Closest to RHS 137A.

*Immature leaf, lower surface.*—Closest to RHS 137D.

*Mature leaf, color upper surface.*—Closest to RHS 137A.

*Mature leaf, color lower surface.*—Closest to RHS 137D.

*Length.*—4.4-4.9 cm.

*Width.*—7.2-8.1 cm.

*Shape.*—Reniform.

*Base shape.*—Cordate.

*Apex shape.*—Rounded.

*Margin.*—Crenate.

*Texture upper side.*—Hirsute.

*Texture lower side.*—Hirsute.

*Leaf zonation.*—Is not present.

*Color of veins, upper surface.*—Mostly indistinct from foliage color.

*Color of veins, lower surface.*—Mostly indistinct from foliage color.

*Pattern of veining.*—Palmate.

*Petiole color.*—RHS 138B.

*Petiole length.*—6.2-7.0 cm.

*Diameter of petiole.*—0.2 cm.

*Strength of petiole.*—Moderately strong.

*Texture.*—Moderately smooth and hirsute.

*Arrangement.*—Typical.

Stem:

*Quantity of branches.*—4-5.

*Color of stem.*—RHS 137B to RHS 137C.

*Length of stem.*—10-12.0 cm.

*Diameter.*—0.6 cm.

*Length of internodes.*—0.5-1.0 cm.

*Texture.*—Hirsute.

Peduncle:

*Color of peduncle.*—RHS 137B to RHS 137C.

*Length of peduncle.*—7-8.0 cm.

*Peduncle diameter.*—0.25 cm.

*Texture.*—Hirsute, pilose.

*Strength of peduncle.*—Moderately strong.

Pedicel:

*Color of pedicel.*—RHS 137C, with anthocyanins of about RHS 178B to RHS 178C at the pedicel apex under the floret.

*Length of pedicel.*—2.1-3.0 cm.

*Diameter of pedicel.*—0.15 cm.

*Texture.*—Hirsute, pilose.

*Strength of pedicel.*—Moderately strong.

Bud (just before opening):

*Color.*—RHS N57A but a little darker and more purple.

*Length.*—1.5-1.7 cm.

*Width.*—0.5-0.7 cm.

*Shape.*—Elliptical.

*Texture.*—Smooth.

Inflorescence:

*Type.*—Umbel; semi-spherical or nearly semi-spherical.

*Duration of flowering.*—Continuous upon commencement.

*Lastingness of individual flowers.*—7-9 days at 18° C. temperature.

*Number of inflorescences per plant.*—10-15, with 4 immature umbels in various sizes.

*Fragrance.*—None.

*Umbel diameter.*—9-10.0 cm.

*Umbel depth.*—5.5-6.0 cm.

Corolla:

*Form.*—Single.

*Number of petals.*—5.

*Diameter of flower.*—4.5-4.9 cm.

*Depth of flower.*—1.5-2.0 cm.

*Color upper petals, upper surface.*—RHS N66C overlaid with a bold blotch of closest to RHS N66A, and a base of RHS N155B and veins of between RHS 60B and RHS 61B.

*Color upper petals, lower surface.*—RHS 67C with mid-veins of RHS 59B.

*Length of upper petals.*—2.7-2.9 cm.

*Width of upper petals.*—1.5-1.8 cm.

*Color lower petals, upper surface.*—RHS N66C overlaid with a bold blotch of closest to RHS N66A, and a base of between RHS N66B and RHS 66C and veins of between RHS 60B and RHS 61B.

*Color lower petals, lower surface.*—RHS 67C with mid-veins of RHS 59B.

*Length of lower petals.*—2.7-2.8 cm.

*Width of lower petals.*—2.1-2.2 cm.

*Petal shape.*—Spathulate.

*Apex shape.*—Rounded.

*Margin.*—Entire.

*Base.*—Cuneate.

*Petal texture, upper surface.*—Papillose.

*Petal texture, lower surface.*—Papillose.

*Number of petaloids.*—None present.

Calyx:

*Number of sepals.*—5.

*Color of sepals.*—RHS 146B.

*Length of sepals.*—1-1.1 cm.

*Width of sepals.*—0.3-0.35 cm.

*Sepal shape.*—Lanceolate.

*Apex shape.*—Acute.

*Margins.*—Mostly fused.

*Texture, upper surface.*—Glabrous.

*Texture, lower surface.*—Hirsute, glandular hairs.

Reproductive organs:

*Gynoecium*.—Pistil: 1. Length: 0.7-0.8 cm. Style color: RHS 155C. Style length: 0.5-0.7 cm. Stigma color: RHS 61B. Sigma type: 5-parted. Ovary color: Closest to RHS 149D, though some are lighter. Ovary length: 0.4 cm. Ovary diameter: 0.15 cm.

*Androecium*.—Number of stamens: About 8-10; though many are not fully formed or developed. Color of filaments: RHS 155C with between RHS 61B and RHS 61C at the apex. Length filaments: 0.3-0.6 cm. Anther color: Closest to RHS 48A. Length of anthers: 0.2 cm. Color of pollen: RHS N25A. Pollen amount: Medium. Fertility/Seed set: Moderate seed set. Disease/Pest resistance: Has not been determined to date.

What is claimed is:

1. A new and distinct variety of *Pelargonium* plant named 'PEQZ0007' substantially as illustrated and described herein.

* * * * *